United States Patent [19]

Brunet

[11] Patent Number: 5,102,397
[45] Date of Patent: Apr. 7, 1992

[54] SAFETY SYRINGE FOR TAKING BLOOD SAMPLES AND FOR INJECTIONS

[76] Inventor: Jean-Louis Brunet, 51-53 Rue du Commandant Charcot, Sainte-Foy-les-Lyon, France, 69110

[21] Appl. No.: 555,512
[22] PCT Filed: Mar. 24, 1989
[86] PCT No.: PCT/FR89/00137
  § 371 Date: Aug. 10, 1990
  § 102(e) Date: Aug. 10, 1990
[87] PCT Pub. No.: WO89/09076
  PCT Pub. Date: Oct. 5, 1989

[30] Foreign Application Priority Data

Mar. 29, 1988 [FR] France .................. 88 04410

[51] Int. Cl.⁵ .............................................. A61M 5/32
[52] U.S. Cl. ................................. 604/192; 604/241; 128/764
[58] Field of Search .............. 604/192, 198, 239–241, 604/263, 272–274; 128/763–765, 768

[56] References Cited

U.S. PATENT DOCUMENTS

| 1,125,887 | 1/1915 | Schimmel | 604/192 X |
| 2,290,857 | 7/1942 | Booye et al. | 604/272 X |
| 2,607,347 | 8/1952 | Kleiner | 128/764 |
| 2,854,976 | 10/1958 | Heydrich | 604/263 X |
| 3,040,743 | 6/1962 | Naess | 604/192 X |
| 3,658,001 | 4/1972 | Hall | 604/192 |
| 3,687,296 | 8/1972 | Spinosa et al. | 128/764 X |
| 3,884,230 | 5/1975 | Wulff | 604/198 |
| 4,280,509 | 7/1981 | Bethkenhagen et al. | 128/764 X |
| 4,819,659 | 4/1989 | Sitar | 128/764 |
| 4,878,904 | 11/1989 | Callaway | 604/273 |
| 4,943,281 | 7/1990 | Kothe | 604/192 |
| 4,994,046 | 2/1991 | Wesson et al. | 604/198 |

FOREIGN PATENT DOCUMENTS

| 8800767 | 7/1988 | Fed. Rep. of Germany | 604/198 |
| 2243705 | 4/1975 | France | 604/192 |
| 1096439 | 12/1967 | United Kingdom | 604/272 |

Primary Examiner—John D. Yasko
Assistant Examiner—Adam J. Cermak
Attorney, Agent, or Firm—Dowell & Dowell

[57] ABSTRACT

A protective device for intravenous needles which includes a needle protector which extends from an injection or collection syringe tube and which has an outer end portion having a groove defined therein in which the tip of a needle is normally seated and wherein the needle is mounted to one end of a hollow pliable sleeve which is bendable from a first orientation in which the needle is seated within the groove to a second orientation whereby the needle is oriented for intravenous placement.

4 Claims, 1 Drawing Sheet

SAFETY SYRINGE FOR TAKING BLOOD SAMPLES AND FOR INJECTIONS

BACKGROUND OF THE INVENTION

1. Field of the Invention

The present invention relates to an improved technical device for taking blood samples and for injections, aiming jointly place at protecting the users from possible accidents by pricking or injury with a soiled needle and at allowing a reflux of the blood through the needle during its penetration into the vein, thus performing, by the same mechanism, two functions non-existent in systems of sampling blood employing vacuum tubes for collecting multiple blood samples. A third advantage brought by the invention should, furthermore, be noted, represented by the fact that the intravenous needle lies parallel to the plane of the skin when the system is in position of penetration of the needle on the arm before puncture, while in existing systems, the needles extending at an angle to the plane of the skin which is often awkward for the user who wishes to take a blood sample.

The first, safety function of protecting a user from the risk of injury by the soiled needle is fundamental, being given the present risk represented by diseases transmissible by the blood.

The concept of the system according to the invention allows by the same mechanism the presentation of the needle parallel to the plane of the skin of during the taking of a blood sample and the visual reflux of the blood in the needle (2nd function) during its intravenous penetration, thus giving the operator a much facilitated means for effecting his/her samplings without any risk of pricking and contact with the blood, while the position of the hand holding the system remains very natural.

2. History of the Related Art

It will be recalled that U.S. Pat. No. 3,658,061 (J. P. HALL) describes a protection device applied to a needle intended for the placing of a catheter, which needle, after the catheter has been placed in position and after it has been withdrawn from the vein, remains around the catheter on the patient's body as long as the catheter is functioning. In order to immobilize the needle and to cover its tip for the purpose of avoiding any risk of injuring the patient, there is provided, according to the above-mentioned document, a deformable protector which presents a groove in which the needle is retracted.

SUMMARY OF THE INVENTION

The device according to the invention comprises, as in the prior art, a needle adapted to retract in the groove of a protector, but the latter and the needle are mounted on a straight, supple, elastic sleeve fixed with the protector to the front part of the vacuum tube support. This sleeve, thanks to its suppleness and elasticity, will make it possible to pass, with an angular-curvilinear movement caused by pressure from the operator's finger, from the position of protection of the needle within the groove to the position of intravenous penetration, the return to safety position being effected by its elasticity.

The reflux of the blood in the system after intravenous penetration of the needle is obtained by the creation of a vacuum within the sleeve before intravenous penetration of the needle when the operator, having just injected, releases the sleeve which he/she had pressed to bring the needle into position of penetration in the vein, having thus previously driven out part of the air contained in the sleeve. The blood will be forced into the sleeve which, being translucent, will show the operator that the needle is well positioned in the patient's vein.

The device according to the invention is not only adaptable to blood sampling systems employing vacuum tubes, but also to conventional syringes.

Figure 1:
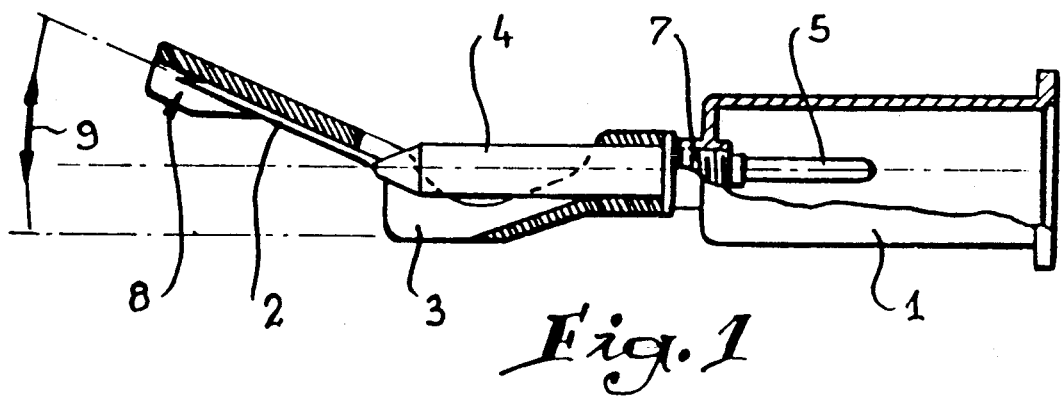
FIG. 1 is a longitudinal section showing the device according to the invention in safety position.
Figure 2:
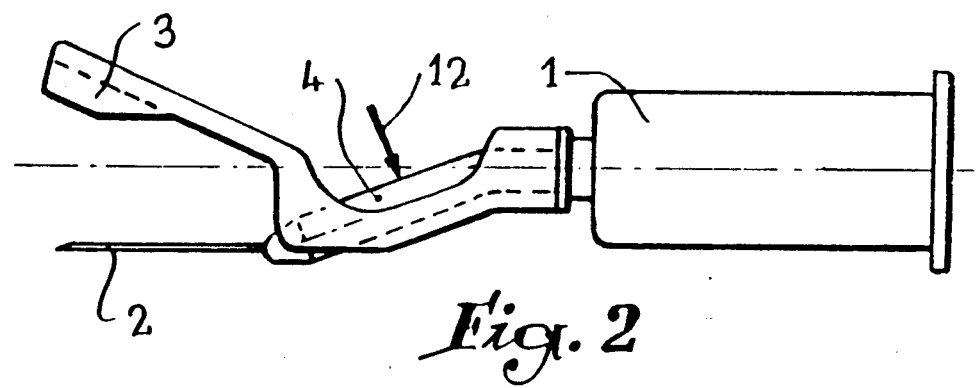
FIG. 2 shows this device in position of penetration of the needle.

The device shown in FIG. 1 includes a vacuum recipient support 1 assembled with the needle protector 3 by a thread 7. The protector 3 includes at its end a groove 8 in which a tip of the needle 2 is housed.

Figure 3:
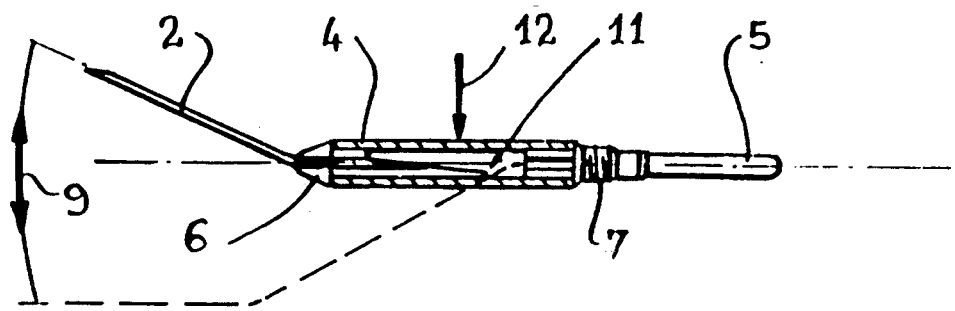
FIG. 3 is a longitudinal section through the elastic sleeve of the present invention and showing an angulated needle.

FIG. 3 shows the needle 2 mounted on its base 6 forming an angle of about 155° with the axis of the elastic straight sleeve 4. The base 6 is mounted within one end of the sleeve 4.

In one embodiment, it is the needle which is incurved at its base; in another embodiment (not shown) it is the base which is incurved, the needle being straight.

FIG. 3 also shows the monitoring chamber 11 inside the straight elastic sleeve 4 where the reflux of the blood is produced and the penetration member 5 to which the sleeve 4 is mounted and which is insertable into the vacuum recipients comprising a needle oriented in opposite direction and covered with a supple cap.

Finally, FIG. 3 shows the angular-curvilinear movement along 9 of the supple, elastic, straight sleeve 4 obtained by the pressure of the operator's finger along 12; the release of this pressure when the needle is in intravenous position provokes suction of the blood inside the sleeve, indicating the correct position of the needle in the patient's vein. If the blood does not appear in chamber 11, this means that the needle is not correctly engaged in the vein.

When the necessary quantity of blood has been taken, it suffices to withdraw the needle from the vein. As soon as the needle tip has left the vein, it will return to its initial position in the groove of the protector thanks to the sleeve which, by its elasticity, immediately returns automatically to its straight position without any additional manipulation by the operator.

The characteristic of the device according to the invention is that of being extremely simple, giving the users a much facilitated means for taking a blood sample while ensuring complete safety.

It goes without saying that the invention is not limited to the sole embodiment of this process described hereinabove by way of example; it covers, on the contrary, all the variants without departing from the scope of the invention.

I claim:

1. A protective device for intravenous needles of the type used with injection and collection syringe tubes comprising, a hollow sleeve having first and second ends, means for connecting said first end to the syringe tube, a needle having a base portion and a tip portion, said base portion of the needle being mounted to said second end of said sleeve, said sleeve being formed of an elastic material so that said second end thereof is resiliently moveable upon the application of pressure from a first orientation relative to the syringe tube to a second orientation relative to the syringe tube, a protective means having a first end for mounting to the syringe tube and a second end extending outwardly beyond said tip of the needle, groove means formed along said second end of said protection means in which the needle is seated when said sleeve is in said first orientation, an opening in said protective means through which pressure may be applied to said sleeve to urge said sleeve from said first orientation to said second orientation, and said sleeve being automatically returnable to said first orientation upon the removal of pressure so that said tip of the needle is seated within said groove of said protective means.

2. The protective device of claim 1 in which said sleeve defines an inner chamber which is in communication with said base portion of the needle, said chamber including side wall portions which are translucent so that a visual monitoring of said chamber is permitted.

3. The protective device of claim 2 in which said base portion of the needle is curved so that an axis taken along said base portion is positioned at an angle with respect to an axis taken along said tip portion thereof.

4. The protective device of claim 1 in which said protective means includes an intermediate portion between said first and second ends, said intermediate portion including a lower wall which tapers outwardly with respect to said second end thereof, said sleeve being spaced with respect to said lower wall of said intermediate portion of said protective means when in said first orientation and being generally in engagement with said lower wall of said intermediate portion of said protective means when in said second orientation.

* * * * *